(12) United States Patent
Kuechler et al.

(10) Patent No.: US 7,304,197 B2
(45) Date of Patent: Dec. 4, 2007

(54) RECYCLING OXYGENATE-RICH STREAMS IN OXYGENATE-TO-OLEFIN PROCESSES

(75) Inventors: Keith H. Kuechler, Friendswood, TX (US); Jeffrey L. Brinen, League City, TX (US); James Richardson Lattner, Seabrook, TX (US); Allen Scott Gawlik, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 392 days.

(21) Appl. No.: 10/720,505

(22) Filed: Nov. 24, 2003

(65) Prior Publication Data

US 2005/0113623 A1    May 26, 2005

(51) Int. Cl.
    *C07C 1/00*    (2006.01)
(52) U.S. Cl. ...................... 585/640; 585/639
(58) Field of Classification Search ........ 585/638–640, 585/809
    See application file for complete search history.

(56) References Cited

U.S. PATENT DOCUMENTS

| | | | |
|---|---|---|---|
| 4,387,263 A | 6/1983 | Vogt et al. ................ | 585/640 |
| 5,714,662 A | 2/1998 | Vora et al. | |
| 5,744,680 A * | 4/1998 | Mulvaney et al. .......... | 585/640 |
| 5,817,906 A | 10/1998 | Marker et al. | |
| 6,121,504 A | 9/2000 | Kuechler et al. .......... | 585/640 |
| 6,403,854 B1 | 6/2002 | Miller et al. ............... | 585/638 |
| 6,441,261 B1 | 8/2002 | Kuechler et al. .......... | 585/639 |
| 6,459,009 B1 | 10/2002 | Miller et al. ............... | 585/809 |
| 6,482,998 B1 * | 11/2002 | Kuechler et al. ........... | 585/638 |
| 2003/0130555 A1 | 7/2003 | Cheng et al. ............... | 585/804 |

FOREIGN PATENT DOCUMENTS

| | | |
|---|---|---|
| EP | 0 060 103 | 9/1982 |
| EP | 0 065 112 | 11/1982 |
| WO | WO 03/048085 | 6/2003 |

OTHER PUBLICATIONS

Thomson Derwent Abstract for EP 0 065 112, Nov. 24, 1982 entitled "Olefins".
U.S. Appl. No. 10/712,953, filed Nov. 12, 2003, Xu et al.
U.S. Appl. No. 10/712,668, filed Nov. 12, 2003, Xu et al.
Anderson, James A. et al, *"Production of Light Olefins from Methanol or Natural Gas"*, UOP Petrochemicals, ICIS-LOR World Olefin Conference, Antwerp, Oct. 2001 (slide 13).

* cited by examiner

Primary Examiner—Glenn Caldarola
Assistant Examiner—In Suk Bullock (57) ABSTRACT

A process and apparatus are provided for converting oxygenate to olefins which comprises: contacting a feedstock comprising oxygenate with a catalyst comprising a molecular sieve under conditions effective to produce a vaporous product comprising the olefins, water and unreacted oxygenate; condensing the vaporous product to provide a liquid stream rich in the water and unreacted oxygenate, and an olefins-rich vapor stream; introducing at least part of the liquid stream to a feed tray in a fractionation tower which provides an oxygenate-rich overhead product and a water-rich liquid bottoms product; providing a liquid, oxygenate-rich stream comprising at least about 20 wt % oxygenate above the feed tray; and passing the olefins-rich vapor stream through a recovery train to recover at least some of the olefins.

61 Claims, 1 Drawing Sheet

RECYCLING OXYGENATE-RICH STREAMS IN OXYGENATE-TO-OLEFIN PROCESSES

FIELD

The present invention relates to recycling oxygenate-rich streams in oxygenate-to-olefin processes (e.g., MTO), etc.

BACKGROUND

Olefins are traditionally produced from petroleum feedstocks by catalytic or steam cracking processes. These cracking processes, especially steam cracking, produce light olefin(s), such as ethylene and/or propylene, from a variety of hydrocarbon feedstocks. Ethylene and propylene are important commodity petrochemicals useful in a variety of processes for making plastics and other chemical compounds.

The petrochemical industry has known for some time that oxygenates, especially alcohols, are convertible into light olefin(s). There are numerous technologies available for producing oxygenates including fermentation or reaction of synthesis gas derived from natural gas, petroleum liquids or carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Other known syngas production processes include conventional steam reforming, autothermal reforming, or a combination thereof.

An important type of alternate feed for the production of light olefins is oxygenate, such as, for example, alcohols, particularly methanol and ethanol, dimethyl ether (DME), methyl ethyl ether, diethyl ether, dimethyl carbonate, and methyl formate. Many of these oxygenates may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for light olefin production. Methanol, the preferred alcohol for light olefin production, is typically synthesized from the catalytic reaction of hydrogen, carbon monoxide and/or carbon dioxide in a methanol reactor in the presence of a heterogeneous catalyst. For example, in one synthesis process methanol is produced using a copper/zinc oxide catalyst in a water-cooled tubular methanol reactor. The preferred process for converting a feedstock containing methanol into one or more olefin(s), primarily ethylene and/or propylene, involves contacting the feedstock with a catalyst composition.

The catalysts used to promote the conversion of oxygenates to olefins are molecular sieve catalysts. Because ethylene and propylene are the most sought after products of such a reaction, research has focused on what catalysts are most selective to ethylene and/or propylene, and on methods for increasing the life and selectivity of the catalysts to ethylene and/or propylene.

Catalytic processes utilizing fluidized bed technology for conversion of hydrocarbon or oxygenates involving gas-solids contacting are widely used in industry for productions of petroleum-based fuels, chemical feed stocks and other industrial materials. The gaseous reactants are contacted with solid catalyst particles to provide gaseous products. Such processes often use continuous catalytic reactor unit operations, requiring catalyst regeneration at high temperature. FCC, MTO and other processes usually employ oxidative regeneration to remove coke or other carbonaceous deposits from spent or equilibrium catalysts.

The hot vaporous product from the reactor, which contains light olefins, unconverted oxygenates, by-product oxygenates, and large amounts of water can be condensed in a suitable condensing means such as a quench tower, heat exchanger, flash drum, primary fractionator or other suitable device, to provide a mixed oxygenate/water stream. This stream can be provided to a fractionation tower designed and operated to separate the unconverted and by-product oxygenates as an overhead stream, and fairly pure water as a bottoms product. The fractionation tower overhead stream is typically mostly methanol (as unconverted feedstock). Given the large amount of water in the fractionation tower feed, the tower is typically quite large with a very high reboiler and condenser duty. Further, there are numerous locations in the overall MTO process which produce streams quite rich in methanol, but also containing certain heavy contaminants such as metal particles or ions. These streams tend to be liquid. It would be beneficial to recycle these methanol rich streams to the MTO reactor following removal of the heavy contaminants, and potentially following vaporization. There is also a desire to make the recycle of these streams as efficient as possible, to save utilities/energy in the overall process.

U.S. Pat. No. 6,121,504 to Kuechler et al. discloses a process for converting oxygenates to olefins with direct product quenching for heat recovery and to improve heat integration.

U.S. Pat. Nos. 6,403,854 and 6,459,009 to Miller et al. disclose a process for converting oxygenate to light olefins with improved heat recovery from reactor effluent streams and improved waste recovery which minimizes overall utility requirements. The reactor effluent is quenched with an aqueous stream in a two-stage process to facilitate the separation of hydrocarbon gases from any entrained catalyst fines, as well as to remove water and any heavy by-products such as $C_6+$ hydrocarbons. A portion of the waste water stream withdrawn from the bottom of the quench tower is recycled to the quench tower at a point above where the reactor effluent is introduced to the quench tower. The references do not appear to teach the use of liquid streams that are substantially free of catalyst fines for treating reactor effluents.

U.S. application Ser. No. 09/998,512, filed Nov. 30, 2001, published Jul. 10, 2003 as United States Patent Application 20030130555, discloses a process for separating oxygenated hydrocarbon from olefin product of oxygenate to olefins reaction. The product is sent to a cooling unit such as a quench tower from which cooled olefin product is separated as an olefin vapor stream. The water containing bottoms stream can be recycled through a heat exchanger for cooling and/or removed from the cooling unit to a first separator, such as a distillation column to provide an oxygenated hydrocarbon product of reduced water content and remaining water as a bottoms product. The olefin vapor stream is compressed and directed to a second separator which provides an olefin vapor product and a liquid oxygenated hydrocarbon containing stream which can be combined with the water containing bottoms stream or directly added to the first separator to provide an oxygenated hydrocarbon product recovered from the first separator that is reduced in water content and can be used as fuel or co-feed for the oxygenate reaction process.

All of the above references are incorporated herein by reference in their entirety.

SUMMARY

In one aspect, the invention relates to a process for converting oxygenate to olefins which comprises: contacting a feedstock comprising oxygenate with a catalyst comprising a molecular sieve under conditions effective to produce a vaporous product comprising the olefins, water and unreacted oxygenate; condensing the vaporous product to provide a liquid stream rich in the water and unreacted oxygenate, and an olefins-rich vapor stream; introducing at least part of the liquid stream to a feed tray in a fractionation tower which provides an oxygenate-rich overhead product and a water-rich liquid bottoms product; providing a liquid, oxygenate-rich stream comprising at least about 20 wt % oxygenate above the feed tray; and passing the olefins-rich vapor stream through a recovery train to recover at least some of the olefins. Typically, the oxygenate can be a $C_1$ to $C_4$ alcohol, say, an oxygenate selected from the group consisting of methanol and ethanol, e.g., methanol. For present purposes, the recovery train comprises one or more of gas compressors, suction drums, distillation columns, methanol absorbers, liquid-liquid absorbers, oxygenate rejection tower, caustic/water wash tower, depropanizers, demethanizers, deethanizers, debutanizer, $C_3$ splitters, $C_2$ splitters, etc., i.e., equipment used to recover the various products of oxygenate conversion, oxygenate by-products and unreacted oxygenates.

In an embodiment of this aspect of the present invention, the liquid, oxygenate-rich stream comprising at least about 20 wt % oxygenate is introduced at more than one level above the feed tray.

In another embodiment, at least two liquid, oxygenate-rich streams comprising at least about 20 wt % oxygenate, are introduced above the feed tray.

In still another embodiment, at least two liquid, oxygenate-rich streams comprising at least about 20 wt % oxygenate, are each introduced at a separate level above said feed tray.

In yet another embodiment, the oxygenate-rich overhead product comprises liquid.

In still yet another embodiment, the oxygenate-rich overhead product comprises vapor.

In yet still another embodiment, the oxygenate-rich overhead product comprises liquid and vapor.

In another embodiment of this aspect of the present invention, at least a portion of the liquid, oxygenate-rich stream comprising at least about 20 wt % oxygenate is the same oxygenate-containing feedstock used for converting oxygenates to olefins.

In another embodiment, at least a portion of the liquid, oxygenate-rich stream comprising at least about 20 wt % oxygenate is derived from the bottoms product of a methanol absorber tower. A methanol absorber tower is typically a column whose upper portion receives a methanol-containing feed, e.g., 99 wt % methanol and 1 wt % water, and whose lower portion receives compressed olefins-containing overheads containing residual oxygenates which are absorbed by the methanol-containing feed which is removed as bottoms from the methanol absorber.

In yet another embodiment, a liquid methanol feedstock can be introduced to the process of the present invention by addition to the methanol absorber tower. Typically, the liquid methanol feedstock comprises at least about 95 wt % methanol, say, at least about 99 wt % methanol. Any conventional contact apparatus, e.g. packed column or plate column, is suitable as a methanol absorber. The recovery of methanol from a saturated solvent, e.g., water, can be achieved by any of the usual methods, in particular by: (1) flashing of the liquid to a lower pressure, (2) heating-up of the liquid up to a temperature level at which methanol desorbs completely or (3) a combination of these two methods.

In still another embodiment, at least a portion of the liquid, oxygenate-rich stream comprising at least about 20 wt % oxygenate is derived from the bottoms product of a liquid-liquid absorber. Liquid-liquid absorbers typically are used to treat two immiscible liquids, one of higher specific gravity, e.g., wash water, introduced at the upper portion of a column and a liquid of lower specific gravity introduced at the lower portion of the column, e.g., an olefins and oxygenate-containing bottoms fraction taken from a fractionating tower. The liquids are intermixed by gravity effects and absorb their respective miscible components from each other to effect extraction. The water sorbs oxygenate from the olefins-containing stream. The olefins-containing stream from which water is extracted is then passed as overhead to, say, a lights tower used to separate lighter hydrocarbons from each other.

In still yet another embodiment, a first cut fractionating tower is employed in the process, which treats olefins-rich overhead derived from a methanol absorber tower. The first cut fractionating tower provides i) an olefins-rich overhead stream which can be further processed in the olefins recovery train and ii) a methanol-rich bottoms stream which is directed to the liquid-liquid absorber.

In another embodiment, wash water is added to the liquid-liquid absorber.

In still another embodiment, the process further comprises treating the olefins-rich overhead from the condenser in at least one suction drum to remove liquid from the olefins-rich overhead, which liquid is directed to the fractionation tower above the feed tray.

In yet another embodiment, the process further comprises compressing the olefins-rich overhead taken from the suction drum.

In still another embodiment, the process further comprises treating the compressed olefins-rich overhead in an additional suction drum to remove liquid from the olefins-rich overhead, which liquid is directed to an upstream suction drum.

In yet still another embodiment, the process further comprises compressing the olefins-rich overhead taken from the additional suction drum.

In another embodiment, the process further comprises introducing the compressed olefins-rich overhead taken from the additional suction drum to a discharge drum whose olefins-rich overhead is directed to a methanol absorber and whose oxygenate-rich bottoms are directed to the additional suction drum.

In still another embodiment, the bottoms product of the methanol absorber tower is directed above the feed tray in the fractionation tower.

In yet another embodiment, the bottoms product of a methanol absorber tower is directed to a suction drum whose bottoms are directed above the feed tray in the fractionation tower.

In yet another embodiment, the condenser is selected from the group consisting of quench tower, heat exchanger, flash drum, and primary fractionator, e.g., a quench tower.

In still yet another embodiment, the liquid, oxygenate-rich stream comprising at least about 20 wt % oxygenate is provided as reflux above the feed tray.

In another embodiment, the liquid, oxygenate-rich stream comprising at least about 20 wt % oxygenate is provided above the feed tray to a reflux drum associated with the fractionation tower from which reflux drum an oxygenate-rich overhead product stream is taken.

In yet another embodiment, the feedstock comprising oxygenate comprises oxygenate-rich overhead product stream taken from the reflux drum.

In still another embodiment, the feedstock comprising oxygenate comprises the oxygenate-rich overhead product from the fractionation tower.

In still yet another embodiment, the oxygenate-rich overhead product from the fractionation tower is used as fuel, e.g., in a combustor or stored as fuel for later use.

In another embodiment, the oxygenate-rich overhead product from the fractionation tower is taken as a liquid drawoff from any tray above the feed tray.

In yet another embodiment, the oxygenate-rich overhead product from the fractionation tower is taken as a vapor drawoff from any tray above the feed tray.

In still another embodiment, the oxygenate-rich overhead product from the fractionation tower is taken as a liquid from a downstream reflux drum.

In still yet another embodiment, the oxygenate-rich overhead product from the fractionation tower is taken as a vapor from a downstream reflux drum.

In yet still another embodiment, the oxygenate-rich overhead product from the fractionation tower is taken as a liquid and vapor from a downstream reflux drum.

In another embodiment, at least one of the group consisting of a) at least one vapor oxygenate-rich overhead product and b) at least one liquid oxygenate-rich overhead product, is taken from the fractionation tower.

In another embodiment, the liquid, oxygenate-rich stream comprising at least about 20 wt % oxygenate comprises liquid blowdown from a vaporizer treating the feedstock prior to the contacting of the feedstock with catalyst in the oxygenate to olefins conversion.

In yet another embodiment, the fractionation tower comprises a condenser which is heat integrated with a vaporizer for the feedstock. By heat integration is meant that heat can be transferred using a suitable heat exchange means between the condenser and the vaporizer as needed to provide efficient operation.

In still another embodiment, the oxygenate-rich overhead product from the fractionation tower is contacted with the catalyst prior to the contacting with feedstock under conditions sufficient to increase the carbon content of the catalyst. Such preliminary treating to increase the carbon content is known as "pre-pooling" which is further described in U.S. application Ser. Nos. 10/712,952, 10/712,668 and 10/712,953 all of which were filed Nov. 12, 2003 and are incorporated herein by reference. Typically, when used to contact catalyst in pre-pooling, at least about 50 wt % of the oxygenate-rich overhead product comprises oxygenates other than methanol.

In another embodiment, the water-rich liquid bottoms product from the fractionation tower contains at least about 99 wt % water.

In yet another embodiment, the oxygenate-rich overhead product from the fractionation tower contains no more than about 50 wt % water, say, no more than about 25 wt % water, typically, no more than about 15 wt % water, e.g., no more than about 10 wt % water.

In still another embodiment, the oxygenate-rich overhead product from the fractionation tower contains at least about 25 wt % methanol plus other oxygenates, say, at least about 50 wt % methanol plus other oxygenates, typically, at least about 75 wt % methanol plus other oxygenates, e.g., at least about 90 wt % methanol plus other oxygenates. In another embodiment, the oxygenate-rich overhead product comprises liquid.

In still another embodiment, the oxygenate-rich overhead product comprises vapor.

In yet another embodiment, the oxygenate-rich overhead product comprises liquid and vapor.

In yet still another embodiment, the fractionation tower comprises packing.

In still yet another embodiment, the fractionation tower comprises a fixed number of actual stages, typically ranging from a condenser at the top as the first stage, to a reboiler at the bottom as the last stage. The feed tray is typically located at about the middle of the actual stages. The liquid, oxygenate-rich stream comprising at least about 20 wt % oxygenate is typically introduced at or above the actual stage corresponding to about 60%, typically about 80%, say about 90%, e.g., about 96%, wherein the first stage corresponds to about 100% and the last stage corresponds to about 0% of the actual stage position. The number of actual stages typically ranges from about 20 to about 100, or from about 30 to about 80, or from about 40 to about 60, say, about 50. As used herein, the terms actual "stages" and actual "trays" are used interchangeably to mean a physical contacting devices, such as bubble cap plates or sieve trays, well known to those skilled in the art, used inside the shell of a fractionation tower to effect fractional distillation.

Alternately, the fractionation tower can comprise a suitable packing as is known in the art, in lieu of or in addition to the actual stages between the first and last actual stages. Such packing comprises suitable material that facilitates intimate gas/liquid contact. The gas/liquid contacting material may include, but is not limited to random packing and structured packing. Examples of these include, Gauze, structured packings such as Metal Max Pak® Mellapak®, Flexipac®, Gempak®, Goodloe®, Sulzer®, or random or dumped packing, such as berl saddles, Intalox® saddles, raschig rings, Pall® rings, and Nutter Rings™. These and other types of suitable gas/liquid contacting equipment are described in detail in Kister, H. Z. Distillation Design, McGraw-Hill, N.Y. (1992), Chapters 6 and 8, the disclosures of which are incorporated herein by reference. Typically such materials are packed to a depth ranging from about 2 ft to about 40 ft (from about 0.6 m to about 12 m), say, from about 4 ft to about 20 ft (from about 1.2 m to about 6 m). The efficacy of the packing material is related to the trays which it replaces or supplements in terms of height equivalent per theoretical plate (HETP), a measure of mass-transfer efficiency. In a packed distillation column, it is the height of packing that makes a separation equivalent to that of a theoretical plate.

HETP is a function of packing type and size, and the physical properties, relative volatilities, distributions and flowrates of the liquid and vapor. Efficiency can best be assessed be means of plant columns in the same service, models scaled from such columns, software models based on data from such columns, or measurements from laboratory models.

A particular packing type and size can be categorized by a typical HETP. As a general rule, one can assume for random packings an HETP of 18 inches for one inch packings; 26 inches for one and a half inch packings; and 36 inches for two inch packings. For structured packings, typical HETPs are 9 inches for 0.25 inch crimp; 18 inches for 0.5 inch crimp; and 33 in. for one inch crimp. Additional guidance can be found in *Chemical Engineering*, April, 1989, "Distillation Column Troubleshooting: Part 2: Packed Columns" by Mark E. Harisson of Tennessee Eastman Co., and John J. France of Glitsch, Inc.

In one manifestation of the present invention, the oxygenate-rich overhead product is a liquid. In another manifestation, the oxygenate-rich overhead product is a vapor. In yet another manifestation, a portion of the oxygenate-rich overhead product is taken as a vapor and the balance taken as a liquid, either discretely or in combination. As used herein, the general term "oxygenate-rich overhead product" refers to either a vapor or liquid state. The term will be modified by either "vapor" or "liquid" to refer specifically to the material in one specific state, e.g., "vapor oxygenate-rich overhead product" referring to the material in the vapor state.

In other manifestations, at least about 10 wt %, or at least about 15 wt %, or at least about 20 wt % of the oxygenate-rich overhead product comprises oxygenates other than methanol.

In another aspect, the present invention relates to an apparatus for converting oxygenates to olefins which comprises: a reactor for contacting a feedstock comprising oxygenate with a catalyst comprising a molecular sieve under conditions effective to produce a vaporous product comprising the olefins, water and unreacted oxygenates; a condenser for condensing the vaporous product to provide a liquid stream rich in the water and unreacted oxygenate, and an olefins-rich vapor stream; a fractionation tower comprising a feed tray for receiving at least part of the liquid stream, and an inlet for receiving a liquid, oxygenate-rich stream comprising at least about 20 wt % oxygenate above the feed tray, the fractionation tower providing an oxygenate-rich overhead product and a water-rich liquid bottoms product; and a recovery train for recovering olefins from the olefins-rich vapor stream.

In another embodiment of this aspect of the present invention, the oxygenate is selected from the group consisting of methanol and ethanol, e.g., methanol. In still another embodiment of this aspect of the invention, the fractionation tower of the apparatus comprises inlets at more than one level above said feed tray for introducing said liquid, oxygenate-rich stream comprising at least about 20 wt % oxygenate.

In yet another embodiment, the fractionation tower of the apparatus comprises at least two inlets above said feed tray for introducing said liquid, oxygenate-rich streams comprising at least about 20 wt % oxygenate.

In still another embodiment, the fractionation tower of the apparatus comprises at least two inlets at separate levels above said feed tray for introducing said liquid, oxygenate-rich streams comprising at least about 20 wt % oxygenate.

In yet another embodiment, the apparatus further comprises a source of the feedstock which can provide at least a portion of the liquid, oxygenate-rich stream comprising at least about 20 wt % oxygenate.

In still another embodiment, the apparatus further comprises a methanol absorber tower from whose bottoms product can be derived at least a portion of the liquid, oxygenate-rich stream comprising at least about 20 wt % oxygenate. The methanol absorber tower typically comprises an inlet for addition of liquid methanol.

In still yet another embodiment, the bottoms product of the methanol absorber tower can be directed above the feed tray in the fractionation tower.

In another embodiment, the bottoms product of the methanol absorber tower can be directed to a suction drum whose bottoms can be directed above the feed tray in the fractionation tower.

In yet another embodiment, the apparatus further comprises a liquid-liquid absorber from whose bottoms product can be derived at least a portion of the liquid, oxygenate-rich stream comprising at least about 20 wt % oxygenate. Typically, the liquid-liquid absorber comprises an inlet for adding wash water.

In yet still another embodiment, the apparatus further comprises a methanol absorber tower which can provide an olefins-rich overhead, a first cut fractionating tower for treating the olefins-rich overhead, the first cut fractionating tower being capable of providing i) an olefins-rich overhead stream and ii) a methanol-rich bottoms stream which can be directed to the liquid-liquid absorber.

In another embodiment, the apparatus further comprises at least one suction drum for removing liquid from the olefins-rich overhead taken from the condenser, which liquid can be directed to the fractionation tower above the feed tray. Typically, the apparatus further comprises a compressor for compressing the olefins-rich overhead taken from the suction drum.

In yet another embodiment, the apparatus further comprises an additional suction drum for removing liquid from the compressed olefins-rich overhead, which liquid can be directed to an upstream suction drum. Typically, the apparatus further comprises an additional compressor for compressing the olefins-rich overhead taken from the additional suction drum.

In still another embodiment, the apparatus further comprises a discharge drum for treating the compressed olefins-rich overhead taken from the additional suction drum, the discharge drum being capable of providing i) an olefins-rich overhead which can be directed to the methanol absorber and ii) oxygenate-rich bottoms which can be directed to the additional suction drum.

In still yet another embodiment, the condenser of the apparatus is selected from the group consisting of quench tower, heat exchanger, flash drum, and primary fractionator, e.g., a quench tower.

In yet still another embodiment, the fractionation tower of the apparatus comprises an inlet for receiving the liquid, oxygenate-rich stream comprising at least about 20 wt % oxygenate as reflux above the feed tray.

In another embodiment, the fractionation tower of the apparatus comprises a reflux drum for receiving above the feed tray the liquid, oxygenate-rich stream comprising at least about 20 wt % oxygenate, from which reflux drum an oxygenate-rich overhead product stream can be taken.

In yet another embodiment, the reflux drum of the apparatus comprises an outlet for directing oxygenate-rich overhead product stream from the reflux drum to above the feed tray. This provides recycling of the overhead to the fractionation tower.

In still another embodiment, the fractionation tower comprises an outlet for directing the oxygenate-rich overhead product from the fractionation tower to the reactor. This provides fractionation tower overhead as feedstock to the oxygenate to olefin reaction.

In yet still another embodiment, the fractionation tower comprises an outlet for directing the oxygenate-rich overhead product from the fractionation tower to a combustor. This provides use of the fractionation tower overhead as a fuel. In another embodiment, the fractionation tower of the apparatus comprises an outlet or outlets for taking oxygenate-rich overhead product as a liquid drawoff from any tray above said feed tray.

In still another embodiment, the fractionation tower of the apparatus comprises an outlet or outlets for taking oxygenate-rich overhead product as a vapor drawoff from any tray above said feed tray.

In yet another embodiment, the apparatus comprises a reflux drum downstream of said fractionation tower, said reflux drum comprising an outlet for taking said oxygenate-rich overhead product as a liquid.

In yet still another embodiment, the apparatus comprises a reflux drum downstream of said fractionation tower, said reflux drum comprising an outlet for taking said oxygenate-rich overhead product as a vapor.

In still yet another embodiment, the apparatus comprises a reflux drum downstream of said fractionation tower, said reflux drum comprising an outlet for taking said oxygenate-rich overhead product as a liquid and a vapor.

In yet another embodiment, the fractionation tower of the apparatus comprises at least one outlet for taking at least one of the group consisting of a) at least one vapor oxygenate-rich overhead product and b) at least one liquid oxygenate-rich overhead product, from said fractionation tower.

In another embodiment, the apparatus further comprises a vaporizer for treating the feedstock prior to the contacting of the feedstock, which vaporizer can provide the liquid, oxygenate-rich stream comprising at least about 20 wt % oxygenate as liquid blowdown from the vaporizer.

In still another embodiment, the apparatus fractionation tower comprises a condenser which is heat integrated with a vaporizer for the feedstock.

In yet another embodiment, the apparatus fractionation tower provides an outlet for directing oxygenate-rich overhead product from the fractionation tower to contact the catalyst at a point before contacting the catalyst with the feedstock can occur. In another embodiment, the fractionation tower of the apparatus comprises packing.

In still yet another embodiment, the apparatus fractionation tower comprises a fixed number of actual stages ranging from a condenser at the top as the first stage to a reboiler at the bottom as the last stage. Typically, the feed tray is located at about the middle of the actual stages. The fractionation tower can comprise an inlet for introducing liquid, oxygenate-rich stream comprising at least about 20 wt % oxygenate, at or above the actual stage corresponding to about 60%, typically, about 80%, say, about 90%, e.g., about 96%, wherein the first stage corresponds to 100% and the last stage corresponds to 0% of the actual stage position.

In another embodiment, the number of actual stages of the apparatus fractionation tower ranges from about from about 20 to about 100, or from about 30 to about 80, or 40 to 60, e.g., about 50.

DETAILED DESCRIPTION

Figure 1:
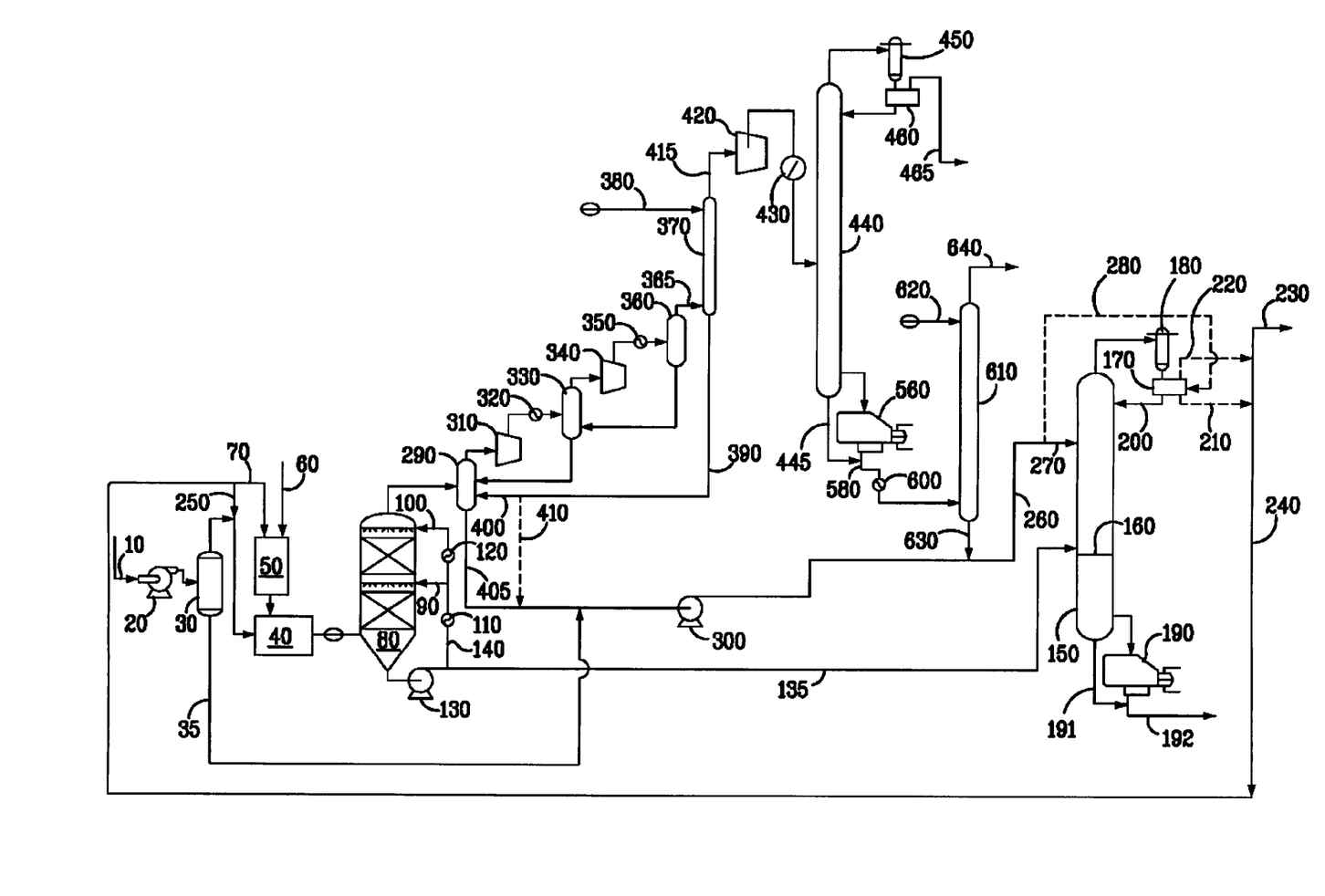
The FIGURE is a schematic process flow diagram depicting certain aspects of the process and apparatus of the invention.

Molecular Sieves and Catalysts Thereof for Use in OTO Conversion

Molecular sieves suited to use for converting oxygenates to olefins (OTO) have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of Zeolite Framework Types,* 5th edition, Elsevier, London, England (2001), which is herein fully incorporated by reference.

Non-limiting examples of these molecular sieves are the small pore molecular sieves of a framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves of a framework-type selected from the group consisting of AFO, AEL, EUO, HEU, FER, MEL, MFI, MTW, MTT, TON, and substituted forms thereof; and the large pore molecular sieves of a framework-type selected from the group consisting of EMT, FAU, and substituted forms thereof. Other molecular sieves have a framework-type selected from the group consisting of ANA, BEA, CFI, CLO, DON, GIS, LTL, MER, MOR, MWW and SOD. Non-limiting examples of the preferred molecular sieves, particularly for converting an oxygenate containing feedstock into olefin(s), include those having a framework-type selected from the group consisting of AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition,* Volume 137, pages 1-67, Elsevier Science, B.V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves utilized in the invention, preferably silicoaluminophosphate molecular sieves have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0

159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZNAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, SAPO$_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak *Handbook of Molecular Sieves*, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanides of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

The molecular sieves useful for oxygenates to olefins conversion processes are synthesized and then made or formulated into catalysts by combining the synthesized molecular sieves with a binder and/or a matrix material to form a molecular sieve catalyst composition. This molecular sieve catalyst composition is formed into useful shaped and sized particles by well-known techniques such as spray drying, pelletizing, extrusion, and the like.

Oxygenate to Olefins Process

In a preferred embodiment of an oxygenate to olefins process, the feedstock contains one or more oxygenates, more specifically, one or more organic compound(s) containing at least one oxygen atom. In the most preferred embodiment, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in an oxygenate to olefins process include lower straight and branched chain aliphatic alcohols and their unsaturated counterparts.

Non-limiting examples of suitable oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or in combination, are converted from a feedstock containing an oxygenate, preferably an alcohol, most preferably methanol, to the preferred olefin(s) ethylene and/or propylene.

There are many processes used to convert feedstock into olefin(s) including various cracking processes such as steam cracking, thermal regenerative cracking, fluidized bed cracking, fluid catalytic cracking, deep catalytic cracking, and visbreaking.

The most preferred process is generally referred to as methanol-to-olefins (MTO). In a MTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 85 weight percent.

Increasing the selectivity of preferred hydrocarbon products such as ethylene and/or propylene from the conversion of an oxygenate using a molecular sieve catalyst composition is described in U.S. Pat. No. 6,137,022 and PCT WO 00/74848 published Dec. 14, 2000, both of which are herein fully incorporated by reference.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see, for example, U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition, is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in, for example, U.S. Pat. Nos. 4,076,796, 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613, filed May 4, 2000 (multiple riser reactor), which are all herein fully incorporated by reference.

In a preferred embodiment, a fluidized bed process or high velocity fluidized bed process includes a reactor system, a regeneration system and a recovery system.

The reactor system preferably is a fluid bed reactor system having a first reaction zone within one or more riser reactor(s) within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol.

Treatment of the oxygenate-containing feedstock prior to its introduction to the oxygenate to olefins conversion reactor may be required to remove non-volatile contaminants.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C., most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WISV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec, e.g., greater than about 15 m/sec. See, for example, U.S. Pat. No. 6,552,240 to Lattner et al., which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See, for example, U.S. Pat. No. 5,952,538, which is herein fully incorporated by reference.

In another embodiment of the process for converting an oxygenate such as methanol to one or more olefin(s) using a molecular sieve catalyst composition, the WHSV is from 0.01 $hr^{-1}$ to about 100 $hr^{-1}$, at a temperature of from about 350° C. to 550° C., and silica to $Me_2O_3$ (Me is selected from Group 13 (IIIA), Groups 8, 9 and 10 (VIII) elements) from the Periodic Table of Elements), and a molar ratio of from 300 to 2500. See, for example, EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001, which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration is in the range of from about 10 psia (68 kPaa) to about 500 psia (3448 kPaa), preferably from about 15 psia (103 kPaa) to about 250 psia (1724 kPaa), and more preferably from about 20 psia (138 kPaa) to about 150 psia (1034 kPaa). Typically, the pressure is less than about 60 psia (414 kPaa).

The preferred residence time of the molecular sieve catalyst composition in the regenerator is in the range of from about one minute to several hours, most preferably about one minute to 100 minutes, and the preferred volume of oxygen in the flue gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The gaseous effluent from the OTO reactor is withdrawn from the disengaging system and is passed through a recovery system. There are many well-known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, for reaction systems such as ethylbenzene manufacture (U.S. Pat. No. 5,476,978) and other derivative processes such as aldehydes, ketones and ester manufacture (U.S. Pat. No. 5,675,041), and other associated equipment, for example, various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a deethanizer, a depropanizer, preferably a wet depropanizer, a wash tower often referred to as a caustic wash tower and/or quench tower, absorbers, adsorbers, membranes, ethylene ($C_2$) splitter, propylene ($C_3$) splitter, butene ($C_4$) splitter, and the like.

Various recovery systems useful for recovering predominately olefin(s), preferably prime or light olefin(s) such as ethylene, propylene and/or butene are described in U.S. Pat. Nos. 5,960,643, 5,019,143, 5,452,581 and 5,082,481, U.S. Pat. No. 5,672,197, 6,069,288, 5,904,880, 5,927,063, and 6,121,503, and 6,293,998, which are all herein fully incorporated by reference.

The reaction products that are withdrawn from the OTO reactor advantageously can be cooled and separated from water, a by-product of the conversion, in a quench tower before the olefin products are recovered. In the quench tower, most of the water is condensed and the light hydrocarbons and light oxygenates removed from the top of the quench tower as an overhead stream and the water removed from the bottom of the quench tower. Water removed from the quench tower comprises some dissolved light hydrocarbons and heavy by-products including heavy oxygenates, e.g., alcohols and ketones, which have a normal boiling point greater than or equal to water and which can be removed by stripping the water from heavy by-products with light gases such as steam or nitrogen. The feedstream passed to an OTO reactor can be refined methanol (essentially pure), or raw methanol comprising up to about 30 weight percent water. The feedstream is advantageously heated and vaporized prior to being charged to the fluidized bed OTO reactor, which requires a considerable amount of energy. Therefore, it is beneficial to recover energy from the reactor effluent and use it to heat and vaporize the feedstream. However, water is substantially the only condensation product in the quench tower. The reaction zone can comprise either a fixed bed or a fluidized reaction zone, but a fluidized reaction zone is preferred.

In the operation of conventional quench systems used in olefin recovery, a large proportion of the water withdrawn from the bottom of the quench tower is cooled, typically by indirect heat exchange, and the cool water is provided to the top of the quench tower, in an operation called a "pumparound." There are typically devices inside the quench tower, such as shed trays, which facilitate the contacting of hot rising vapor with cool falling water to condense water and provide the olefins-rich vapor stream as an overhead product and a liquid stream rich in water as a bottoms product.

The liquid stream rich in water will contain various other materials, typically unreacted oxygenate feedstock, e.g., methanol, and other oxygenates created as byproducts of the oxygenate to olefins reaction, for example, but not limited to, ethanol, ethanal, propanal, acetone, butanone, dimethyl ether, methyl ethyl ether, acetic acid and propionic acid. The proportions of these oxygenates in the liquid stream rich in water may vary widely dependent upon the nature of the oxygenate to olefin reactor, including feedstock, catalyst, WHSV, temperature and pressure, among others things. Further, the proportions of these oxygenates in the liquid stream rich in water may vary widely dependent upon the specifics of the quench tower, such as the pressure, temperature, height of the tower and nature of internals, and pumparound rate, among other things.

Regardless of the exact composition, the liquid stream rich in water will need to undergo further processing to provide components in an appropriate state for use or further treatment, e.g., provide a water stream low enough in organic content for typical water waste treatment, or provide an oxygenate stream low enough in water content for use as fuel or for addition to some point in the oxygenate to olefins process or apparatus.

The present invention introduces oxygenate-rich streams to a section above the feed tray of a water-oxygenate fractionation tower, e.g., water-methanol fractionation tower, used to treat condenser bottoms such as quench tower bottoms, introduced to the fractionation tower at the feed tray. Adding the oxygenate-rich streams to a section above the feed tray of the fractionation tower reduces the condenser duty of the water-oxygenate fractionation tower, while reducing certain heavy contaminants such as metal ions, metal particles or scale such as rust flakes, or catalyst fines, in the oxygenate recycle stream, and vaporizing the oxygenate to provide an oxygenate rich overhead product. The vaporized overhead can be used for recycle to the fractionation tower, recycle to the OTO reactor while unloading the primary methanol vaporization system, or used as fuel.

The present invention provides an OTO effluent containing light hydrocarbons, unconverted and/or by-product oxygenates, and condenses the effluent to provide a liquid stream comprising primarily water and those oxygenates, and a vapor stream primarily comprising light hydrocarbons.

The liquid stream is directed to a fractionation tower operating to separate methanol and other oxygenates as an overhead, e.g., greater than about 20 wt % oxygenates (with the balance being largely water), and substantially pure water as a bottoms stream, typically, greater than about 90 wt % water, say, greater than about 95 wt % water, e.g., greater than about 99 wt % water.

A liquid, oxygenate-rich stream containing at least about 20 wt % oxygenate is directed to the fractionation tower at a point above the feed tray. The liquid, oxygenate-rich can be obtained from any suitable source including from the recovery train of the OTO process itself, or outside the process, e.g., from the same sources of oxygenate feedstocks which are converted by OTO. Introduction of the liquid, oxygenate-rich stream above the feed tray allows the stream to serve as reflux in the fractionation tower and thus reduces the condenser duty of the fractionation tower. Introduction of the liquid, oxygenate-rich stream above the feed tray can include introducing the stream to a reflux drum positioned at the top of the tower, or to a tray within the tower positioned above the feed tray. The latter embodiment provides removal of heavy contaminants by vaporizing the liquid stream at some point in the tower and forcing the heavy contaminants down the tower in the liquid, thus providing an overhead stream reduced in heavy contaminants. Alternatively, the liquid, oxygenate-rich stream is provided directly to the reflux drum associated with the fractionation tower.

More than one liquid, oxygenate-rich stream may be directed to the fractionation tower to more than one point above the feed tray. Alternatively, if desired, a given liquid, oxygenate-rich stream may be apportioned and directed to the fractionation tower to more than one point above the feed tray.

The oxygenate-rich overhead product from this fractionation tower (to which the liquid, oxygenate-rich stream is added above the feed tray) can be taken as a traditional liquid product from the reflux drum, or as a liquid drawoff from any tray above the feed tray, preferably from a tray above the highest point into which liquid, oxygenate-rich stream is added. Alternatively, the oxygenate-rich overhead product may be taken as a vapor from the reflux drum, in what is known as partial condenser operation, or as a vapor drawoff from any tray above the feed tray, preferably from a tray above the highest point into which liquid, oxygenate-rich stream is added . Further, both a vapor and a liquid oxygenate-rich overhead product may be taken from the reflux drum, in what is known as mixed condenser operation, or vapor and liquid oxygenate-rich overhead product may be taken as a drawoff from any tray or trays above the feed tray, preferably from a tray or trays above the highest point at which liquid, oxygenate-rich stream is added. Of course, more than one vapor, or more than one liquid oxygenate-rich overhead product, or more than one of each may be taken from the fractionation tower.

Liquid, methanol-rich streams used in the present invention can be obtained from various sources, including one or more of those noted below.

In one embodiment, the invention utilizes a liquid, methanol-rich stream which is taken from a liquid methanol absorption/wash unit operation for treating vaporous overhead from the condenser, e.g., quench tower, used to treat hot, vaporous, OTO effluent. The unit separates, as bottoms, the water and optionally, by-product oxygenates from the light hydrocarbons-containing overhead. These bottoms can be used as the liquid, methanol-rich stream.

Another embodiment utilizes a methanol-rich stream which is taken as bottoms from a liquid-liquid absorber, say, a methanol absorption/wash unit, used to treat the bottoms from a first cut fractionation tower fed by the vaporous overhead of the aforementioned condenser, which first cut fractionation tower provides a bottoms product enriched in by-product oxygenates.

Still another embodiment provides a liquid, methanol-rich stream, which is derived from a unit operation serving to vaporize feedstock methanol for introduction to the reactor, e.g., a liquid blowdown from a methanol feedstock vaporization flash drum.

Yet another embodiment provides a liquid, methanol-rich stream which is primary methanol feedstock to the reactor/vaporization system of the OTO process. Such feedstock can be taken directly from tankage or a methanol production unit.

The oxygenate-rich overhead product of the oxygenate-water (methanol-water) fractionation tower can be used for various purposes, including as a fuel, as feedstock to the OTO reactor along with the primary oxygenate feedstock. If the oxygentate-rich overhead product is taken as a vapor in a partial condenser operation, this provides vaporized methanol/oxygenate feed to the reactor with virtually no incremental heat input beyond that already required in the reboiler of the methanol-water fractionation tower, with no incremental heat load in the primary feed vaporization section.

In another aspect, the condenser of the fractionation tower is heat integrated with the vaporization of the primary oxygenate feedstock, e.g., by one or more heat exchangers.

In yet another aspect, the overhead product of the fractionation tower is contacted with catalyst to increase the carbon content thereof prior to the catalyst being used to convert oxygenate to olefins.

Various embodiments of the present invention introduce the liquid, oxygenate-rich stream to the oxygenate-water fractionation tower on a tray that is typically no more than 30 trays, or no more than 20 trays, say, no more than 10 trays, e.g., no more than 5 trays or even no more than 2 trays, below a condenser, the condenser being considered as the first tray at the top of the tower with a reboiler at the bottom of the tower considered as the last or nth tray. In general, the closer the liquid, oxygenate-rich stream is introduced to the condenser/reflux drum, the greater the energy savings, given a composition of the liquid, oxygenate-rich stream which is similar or higher in oxygenate, e.g., methanol, content than the desired overhead product. In contrast, liquid, methanol-rich streams having lower methanol contents typically provide increased energy savings as they are introduced farther away from the condenser/reflux drum.

Referring to the FIGURE, embodiments of the method and apparatus of the present invention are depicted in a schematic process flow sheet. A substantially liquid oxygenated feed in line 10 is drawn by a pump 20 to a vaporizer 30 which provides a liquid oxygenated blowdown via line 35, and a vaporous oxygenated feed to a reaction zone 40 which receives catalyst from a zone 50 which takes in catalyst via line 60 and optionally receives oxygenate from line 70 for pre-pooling treatment of the catalyst to increase its carbon content. The reaction zone provides a hot stream of vaporous product containing olefins, other hydrocarbons, water, unreacted oxygenate and oxygenate by-products which is directed to a condenser, viz, quench tower 80 wherein the hot, vaporous product is condensed by contacting with liquid water introduced to the quench tower via lines 90 and 100, heat being removed from the water via heat exchangers 110 and 120. The quench tower provides a bottoms liquid stream rich in water and unreacted oxygenate, a portion of which is recycled to the tower by pump 130 via line 140 and another portion of which is directed to a fractionation tower 150 via line 135 to feed tray 160. The fractionation tower which can be operated with a condenser pressure ranging from about 7 to about 1723 kpag (about 1 to about 250 psig), or from about 69 to about 1033 kpag (about 10 to about 150 psig), or from about 345 to about 689 kpag (about 50 to about 100 psig), say about 517 kpag (about 75 psig), comprises 50 actual stages, including condenser 180 associated with reflux drum 170 as stage 1 (which receives fractionation tower overhead) and reboiler 190 as stage 50, which provides a purified water stream via line 192. Reboiler 190 can be bypassed via line 191. The feed tray 160 is located at about stage 25. If column packing is substituted for actual trays then the feed would be introduced to the fractionation tower at proportionally the same location, i.e., about midway through the packed column. Other inlets and outlets in a packed column would be similarly located in relation to the corresponding actual trays for which they are substituted. Liquid from reflux drum 170 can be directed back to the upper portion of the fractionation tower via line 200 as reflux, and/or removed from the process via line 210 as liquid oxygenate-rich overhead product. Alternatively, vapor oxygenate-rich overhead product may be taken from the reflux drum 170 via line 220, instead of or in addition to the liquid oxygenate-rich overhead product via line 210. The highly concentrated methanol and oxygenates in the oxygenate-rich overhead product, as either the liquid in line 210 or the vapor in line 220 or both, can be removed via line 230 and/or recycled via line 240 to the process as oxygenated feed via line 250 and/or via line 70 to be contacted with catalyst prior to oxygenate to olefin conversions for prepooling of the catalyst.

In order to reduce the condenser duty of the fractionation tower 150, a liquid, oxygenate-rich stream comprising at least about 20 wt % oxygenate is introduced to the tower at a point above the feed tray 160 via line 260 and 270. In one aspect, the liquid, oxygenate-rich stream can be added to condenser 170 at actual stage 1 via line 280. Various sources for the liquid, oxygenate-rich stream are found within the process as will be described below.

Olefins-rich vapor stream is taken as overhead from quench tower 80 to suction drum 290 which provides a liquid, oxygenate-rich stream as bottoms in line 405, which is further directed via pump 300 and line 260 to the fractionation tower 150. The vaporous overhead from suction drum 290 is passed via compressor 310 and heat exchanger 320 to suction drum 330 whose liquid bottoms are directed to suction drum 290 while its overhead is passed via compressor 340 and heat exchanger 350 to discharge drum 360 whose liquid bottoms are directed to suction drum 330 while the discharge drum overhead is directed to methanol absorber 370 via line 365. The methanol absorber extracts oxygenates from the olefins-containing overhead received at the lower portion of the methanol absorber from the material in line 365. A liquid methanol feed is introduced to the upper portion of the methanol absorber via line 380. The methanol absorber bottoms are a liquid, oxygenate-rich stream above 20 wt. % oxygenates which can be directed (using a pump, as necessary) to suction drum 290 via lines 390 and 400 and/or via line 410 directly to line 260, and thence introduced to the fractionation tower 150 above the feed tray. The total sources of line 260 provide a liquid, oxygenate-rich stream comprising at least about 20 wt % oxygenate, although all the respective sources need not individually meet this requirement.

The overhead from the methanol absorber 370 is directed via line 415 to compressor 420 and heat exchanger 430 to the middle of first cut fractionating tower 440 to create a first cut tower olefins-rich overhead stream 465 via reflux drum 460 and condenser 450. The first cut tower olefins-rich overhead stream 465 can be further processed to create high purity olefins, such as polymer grade ethylene and polymer grade propylene, via methods well known to those skilled in the art, including but not limited to caustic washing for acid gas removal, drying via molecular sieve adsorption, removal of acetylenes and dienes via selective hydrogenation, and additional pumping, compression and fractionation.

The bottoms of the first cut fractionating tower 440 are directed from reboiler 560 via line 580. Reboiler 560 can be bypassed via line 445. First cut tower bottoms are directed via line 580 to heat exchanger 600 and further to the lower portion of liquid-liquid absorber 610 whose upper portion is fed by wash water via line 620. Liquid-liquid absorber 610 provides a liquid washed olefin in line 640 as an overhead and a liquid, oxygenate-rich stream in line 630 as bottoms.

The bottoms in line 630 are also provided to fractionation tower 150 via line 260, as discussed above. The liquid washed olefin stream in line 640 can be further processed to create high purity olefins, such as butylenes or butene-1 comonomer, via methods well known to those skilled in the art, including but not limited to caustic washing for acid gas removal, drying via molecular sieve adsorption, removal of acetylenes and dienes via selective hydrogenation, removal of isobutylene via etherification with methanol, and additional pumping, compression and fractionation.

The TABLE below sets out conditions and compositions for various streams and equipment of the process as described in the Figure, with stream compositions given in weight percent, for an example described next. In this example, the rates for streams 35, 405 and 630 are assumed to be zero. The liquid stream rich in water 135 from quench tower 80 is provided to methanol-water fractionation tower 160 on tray 25 of a total of 50 trays. A vapor oxygenate-rich overhead product is taken from reflux drum 170 (thus serving along with the condenser 180 as tray 1), and no liquid oxygenate-rich overhead product is withdrawn. The bottoms 390 from the methanol absorber 610 provide a liquid, oxygenate-rich stream that is directed to the fractionation tower 150 on tray 8 via lines 410 and 260 (and pump 300). The reboiler duty of the fractionation tower with a liquid, oxygenate-rich stream provided to tray 8 (above the feed tray 25) is 72.58 gigacalories/h (288 MBtu/h) and condenser duty is 27.22 gigacalories/h (108 MBtu/h) which shows an improvement over a comparative arrangement. The comparative arrangement differs by adding the liquid oxygenate-rich stream directly to the feed tray at actual stage 25 along with the liquid stream rich in water (instead of providing the liquid oxygenate-rich stream to tray 8), which has reboiler duty of 74.34 gigacalories/h (295 MBtu/h) and condenser duty of 29.48 gigacalories/h (117 MBtu/h).

The TABLE below sets out conditions and compositions for the various streams of the process of the invention.

TABLE

| Comp. | Stream (wt. %) | | | | | | |
|---|---|---|---|---|---|---|---|
| | 380 | 365 | 390 | 135 | 220 | 192 | 415 |
| $H_2$, $CH_4$, CO, $CO_2$, N | | 1.75 | 0.01 | tr. | tr. | | 1.72 |
| $C_2H_2$, $C_2H_4$, $C_2H_6$ | | 38.59 | 0.03 | tr. | 0.10 | | 37.83 |
| $C_3H_4$, $C_3H_6$, $C_3H_8$ | | 39.03 | 0.47 | 0.01 | 0.27 | | 38.24 |
| $C_4$ Hydrocarbon | | 9.39 | 0.16 | 0.03 | 0.37 | | 9.20 |
| $C_5+$ Hydrocarbon | | 4.39 | 2.50 | 0.02 | 0.25 | | 4.30 |
| $H_2O$ | 0.15 | 0.81 | 31.28 | 92.59 | 11.00 | 99.97 | .01 |
| $CH_3OH$ | 99.85 | 0.63 | 26.29 | 6.13 | 68.88 | 0.01 | 4.42 |
| Other Oxygenates | | 5.41 | 39.26 | 1.21 | 19.13 | 0.02 | 4.28 |
| Rate (klb/hr) | 32,000 | 702,782 | 18,021 | 1,180,039 | 111,760 | 1,086,300 | 716,761 |
| Temp (F.) | 80 | 110 | 96 | 217 | 256 | 328 | 90 |
| Pres (psig) | 80 | 65 | 61 | 100 | 75 | 85 | 60 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for converting oxygenate to olefins which comprises:
    contacting a feedstock comprising oxygenate with a catalyst comprising a molecular sieve under conditions effective to produce a vaporous product comprising said olefins, water and unreacted oxygenate;
    condensing in a condenser said vaporous product to provide a liquid stream rich in said water and unreacted oxygenate, and an olefins-rich vapor stream;
    introducing at least part of said liquid stream to a feed tray in a fractionation tower which provides an oxygenate-rich overhead product and a water-rich liquid bottoms product;
    providing a liquid, oxygenate-rich stream comprising at least about 20 wt % oxygenate above said feed tray, wherein said oxygenate is selected from the group consisting of methanol, ethanol, and a combination thereof; and
    passing said olefins-rich vapor stream through a recovery train to recover at least some of said olefins.

2. The process of claim 1 wherein said oxygenate comprises methanol.

3. The process of claim 1 wherein said liquid, oxygenate-rich stream comprising at least about 20 wt % oxygenate is introduced at more than one level above said feed tray.

4. The process of claim 1 wherein at least two liquid, oxygenate-rich streams comprising at least about 20 wt % oxygenate, are introduced above said feed tray.

5. The process of claim 4 wherein said at least two liquid, oxygenate-rich streams comprising at least about 20 wt % oxygenate, are each introduced at a separate level above said feed tray.

6. The process of claim 1 wherein said oxygenate-rich overhead product comprises liquid.

7. The process of claim 1 wherein said oxygenate-rich overhead product comprises vapor.

8. The process of claim 1 wherein said oxygenate-rich overhead product comprises liquid and vapor.

9. The process of claim 2 wherein at least a portion of said liquid, oxygenate-rich stream comprising at least about 20 wt % oxygenate is said feedstock.

10. The process of claim 2 wherein at least a portion of said liquid, oxygenate-rich stream comprising at least about 20 wt % oxygenate is derived from the bottoms product of a methanol absorber tower.

11. The process of claim 10 wherein liquid methanol feedstock is introduced to the process by addition to said methanol absorber tower.

12. The process of claim 11 wherein said liquid methanol feedstock comprises at least about 95 wt % methanol.

13. The process of claim 11 wherein said liquid methanol feedstock comprises at least about 99 wt % methanol.

14. The process of claim 2 wherein at least a portion of said liquid, oxygenate-rich stream comprising at least about 20 wt % oxygenate is derived from the bottoms product of a liquid-liquid absorber.

15. The process of claim 14 wherein a first cut fractionating tower, which treats olefins-rich overhead derived from a methanol absorber tower, provides i) an olefins-rich overhead stream and ii) a methanol-rich bottoms stream which is directed to said liquid-liquid absorber.

16. The process of claim 14 wherein wash water is added to said liquid-liquid absorber.

17. The process of claim 2 which further comprises treating said olefins-rich overhead from said condenser in at least one suction drum to remove liquid from an olefins-rich overhead which liquid is directed to said fractionation tower above said feed tray.

18. The process of claim 17 which further comprises compressing said olefins-rich overhead taken from said suction drum.

19. The process of claim 18 which further comprises treating said compressed olefins-rich overhead in an additional suction drum to remove liquid from said olefins-rich overhead which liquid is directed to an upstream suction drum.

20. The process of claim 19 which further comprises compressing said olefins-rich overhead taken from said additional suction drum.

21. The process of claim 20 which further comprises introducing said compressed olefins-rich overhead taken from said additional suction drum to a discharge drum whose olefins-rich overhead is directed to a methanol absorber and whose oxygenate-rich bottoms are directed to said additional suction drum.

22. The process of claim 10 wherein said bottoms product of said methanol absorber tower is directed above said feed fray in said fractionation tower.

23. The process of claim 10 wherein said bottoms product of a methanol absorber tower is directed to a suction drum whose bottoms are directed above said feed tray in said fractionation tower.

24. The process of claim 1 wherein said condenser is selected from the group consisting of quench tower, heat exchanger, flash drum, and primary fractionator.

25. The process of claim 1 wherein said condenser is a quench tower.

26. The process of claim 1 wherein said liquid, oxygenate-rich steam comprising at least about 20 wt % oxygenate is provided as reflux above said feed tray.

27. The process of claim 1 wherein said liquid, oxygenate-rich stream comprising at least about 20 wt % oxygenate is provided above said feed tray to a reflux drum associated with said fractionation tower from which reflux drum an oxygenate-rich overhead product stream is taken.

28. The process of claim 27 wherein said feedstock comprising oxygenate comprises oxygenate-rich overhead product stream taken from said reflux drum.

29. The process of claim 1 wherein said feedstock comprising oxygenate comprises said oxygenate-rich overhead product from said fractionation tower.

30. The process of claim 1 wherein said oxygenate-rich overhead product from the fractionation tower is taken as a liquid drawoff from any tray above said feed tray.

31. The process of claim 1 wherein said oxygenate-rich overhead product from the fractionation tower is taken as a vapor drawoff from any tray above said feed fray.

32. The process of claim 1 wherein said oxygenate-rich overhead product from the fractionation tower is taken as a liquid from a downstream reflux drum.

33. The process of claim 1 wherein said oxygenate-rich overhead product from to fractionation tower is taken as a vapor from a downstream reflux drum.

34. The process of claim 1 wherein said oxygenate-rich overhead product from the fractionation tower is taken as a liquid and vapor from a downstream reflux drum.

35. The process of claim 1 wherein at least one of the group consisting of a) at least one vapor oxygenate-rich overhead product and b) at least one liquid oxygenate-rich overhead product, is taken from said fractionation tower.

36. The process of claim 1 wherein said oxygenate-rich overhead product from said fractionation tower is used as fuel.

37. The process of claim 1 wherein said liquid, oxygenate-rich stream comprising at least about 20 wt % oxygenate comprises liquid blowdown from a vaporizer treating said feedstock prior to said contacting of said feedstock.

38. The process of claim 1 wherein said fractionation tower comprises a condenser which is heat integrated with a vaporizer for said feedstock.

39. The process of claim 1 wherein said oxygenate-rich overhead product from said fractionation tower is contacted with said catalyst prior to said contacting with feedstock under conditions sufficient to increase the carbon content of said catalyst.

40. The process of claim 1 wherein said water-rich liquid bottoms product contains at least about 99 wt % water.

41. The process of claim 1 wherein said oxygenate-rich overhead product contains no more than about 50 wt % water.

42. The process of claim 1 wherein said oxygenate-rich overhead product contains no more than about 25 wt % water.

43. The process of claim 1 wherein said oxygenate-rich overhead product contains no more than about 15 wt % water.

44. The process of claim 1 wherein said oxygenate-rich overhead product contains no more than about 10 wt % water.

45. The process of claim 1 wherein said oxygenate-rich overhead product contains at least about 25 wt % methanol plus other oxygenates.

46. The process of claim 1 wherein said oxygenate-rich overhead product contains at least about 50 wt % methanol plus other oxygenates.

47. The process of claim 1 wherein said oxygenate-rich overhead product contains at least about 75 wt % methanol plus other oxygenates.

48. The process of claim 1 wherein said oxygenate-rich overhead product contains at least about 90 wt % methanol plus other oxygenates.

49. The process of claim 39 wherein at least about 10 wt % of said oxygenate-rich overhead product comprises oxygenates other than methanol.

50. The process of claim 1 wherein said oxygenate-rich overhead product comprises liquid.

51. The process of claim 1 wherein said oxygenate-rich overhead product comprises vapor.

52. The process of claim 1 wherein said oxygenate-rich overhead product comprises liquid and vapor.

53. The process of claim 1 wherein said fractionation tower comprises packing.

54. The process of claim 1 wherein said fractionation tower comprises a fixed number of actual stages ranging from a condenser at the top as the first stage to a reboiler at the bottom as the last stage.

55. The process of claim 54 wherein said feed tray is located at about the middle of said actual stages.

56. The process of claim 55 wherein said liquid, oxygenate-rich stream comprising at least about 20 wt % oxygenate is introduced at or above the actual stage corresponding to about 60% wherein the first stage corresponds to about 100% and the last stage corresponds to about 0% of the actual stage position.

57. The process of claim 55 wherein said liquid, oxygenate-rich stream comprising at least about 20 wt % oxygenate is introduced at or above the actual stage corresponding to about 80% wherein the first stage corresponds to about 100% and the last stage corresponds to about 0% of the actual stage position.

58. The process of claim 55 wherein said liquid, oxygenate-rich stream comprising at least about 20 wt % oxygenate is introduced at or above the actual stage corresponding to about 90% wherein the first stage corresponds to about 100% and the last stage corresponds to about 0% of the actual stage position.

59. The process of claim 55 wherein said liquid, oxygenate-rich stream comprising at least about 20 wt % oxygenate is introduced at or above the actual stage corresponding to about 96% wherein the first stage corresponds to about 100% and the last stage corresponds to about 0% of the actual stage position.

60. The process of claim 54 wherein said number of actual stages ranges from about 20 to about 100.

61. The process of claim 54 wherein said number of actual stages ranges from about 40 to about 60.

* * * * *